US005498705A

United States Patent [19]

Oin

[11] Patent Number: 5,498,705
[45] Date of Patent: Mar. 12, 1996

[54] MODIFIED POLYSACCHARIDES HAVING IMPROVED ABSORBENT PROPERTIES AND PROCESS FOR THE PREPARATION THEREOF

[75] Inventor: Jian Oin, Appleton, Wis.

[73] Assignee: Kimberly-Clark Corporation, Neenah, Wis.

[21] Appl. No.: 392,439

[22] Filed: Feb. 22, 1995

[51] Int. Cl.⁶ .............................. C08B 7/00; A61L 15/28
[52] U.S. Cl. .................. 536/20; 536/56; 536/59; 536/62; 536/63; 536/84; 536/87; 536/88; 536/97; 536/102; 536/104; 536/106; 536/111; 536/114; 536/124; 604/358; 427/213.33; 527/300
[58] Field of Search .................. 604/358; 427/213.33; 527/300; 536/20, 56, 59, 62, 63, 84, 87, 88, 97, 102, 104, 106, 111, 114, 124

[56] References Cited

U.S. PATENT DOCUMENTS

| | | | |
|---|---|---|---|
| 3,379,720 | 4/1968 | Reid | 336/87 |
| 3,658,790 | 4/1972 | Bernardin | 536/34 |
| 3,723,413 | 3/1973 | Chatterjee et al. | 536/87 |
| 4,036,588 | 7/1977 | Williams et al. | 8/130.1 |
| 4,043,952 | 8/1977 | Ganslaw et al. | 106/197.2 |
| 4,051,086 | 9/1977 | Reid | 525/154 |
| 4,090,013 | 5/1978 | Ganslaw et al. | 525/327.9 |
| 4,127,944 | 12/1978 | Giacobello | 34/349 |
| 4,295,987 | 10/1981 | Parks | 252/194 |
| 4,333,461 | 6/1982 | Muller | 604/368 |
| 4,373,096 | 2/1983 | Koshugi | 536/20 |
| 4,462,982 | 7/1984 | Samejima et al. | 424/495 |
| 4,493,928 | 1/1985 | Koshugi | 536/20 |
| 4,507,438 | 3/1985 | Obayashi et al. | 525/119 |
| 4,541,871 | 9/1985 | Obayashi et al. | 106/197.2 |
| 4,548,847 | 10/1985 | Aberson et al. | 428/74 |
| 4,582,865 | 4/1986 | Balaza et al. | 524/29 |
| 4,587,308 | 5/1986 | Makita et al. | 525/373 |
| 4,666,975 | 5/1987 | Yamasaki et al. | 524/733 |
| 4,666,983 | 5/1987 | Tsubakimoto et al. | 525/119 |
| 4,689,408 | 8/1987 | Gelman et al. | 536/98 |
| 4,727,097 | 2/1988 | Kobayaski et al. | 523/408 |
| 4,734,478 | 3/1988 | Tsubakimoto et al. | 527/300 |
| 4,758,617 | 7/1988 | Tanioku et al. | 524/413 |
| 4,771,105 | 9/1988 | Shirai et al. | 525/54.23 |
| 4,783,510 | 11/1988 | Saotome | 525/329.7 |
| 4,798,861 | 1/1989 | Johnson et al. | 524/458 |
| 4,973,632 | 11/1990 | Nagasune et al. | 526/200 |
| 5,017,229 | 5/1991 | Burns et al. | 106/162 |
| 5,026,800 | 6/1991 | Kimura et al. | 526/200 |
| 5,128,326 | 7/1992 | Balazs et al. | 514/54 |
| 5,151,264 | 9/1992 | Samain et al. | 424/1.21 |

FOREIGN PATENT DOCUMENTS

0442185A1  8/1991  European Pat. Off. .

Primary Examiner—Douglas W. Robinson
Assistant Examiner—Kathleen Kahler Fonda
Attorney, Agent, or Firm—Thomas J. Mielke; John R. Schenian

[57] ABSTRACT

Disclosed is a method for producing a surface-crosslinked, modified polysaccharide having improved absorption properties. The method involves forming a mixture of water and a crosslinking agent, adding a generally water-soluble, modified polysaccharide to said mixture wherein the surface of the polysaccharide becomes crosslinked, and drying the modified polysaccharide. Also described is a surface-crosslinked, modified polysaccharide having improved absorption properties.

34 Claims, 2 Drawing Sheets

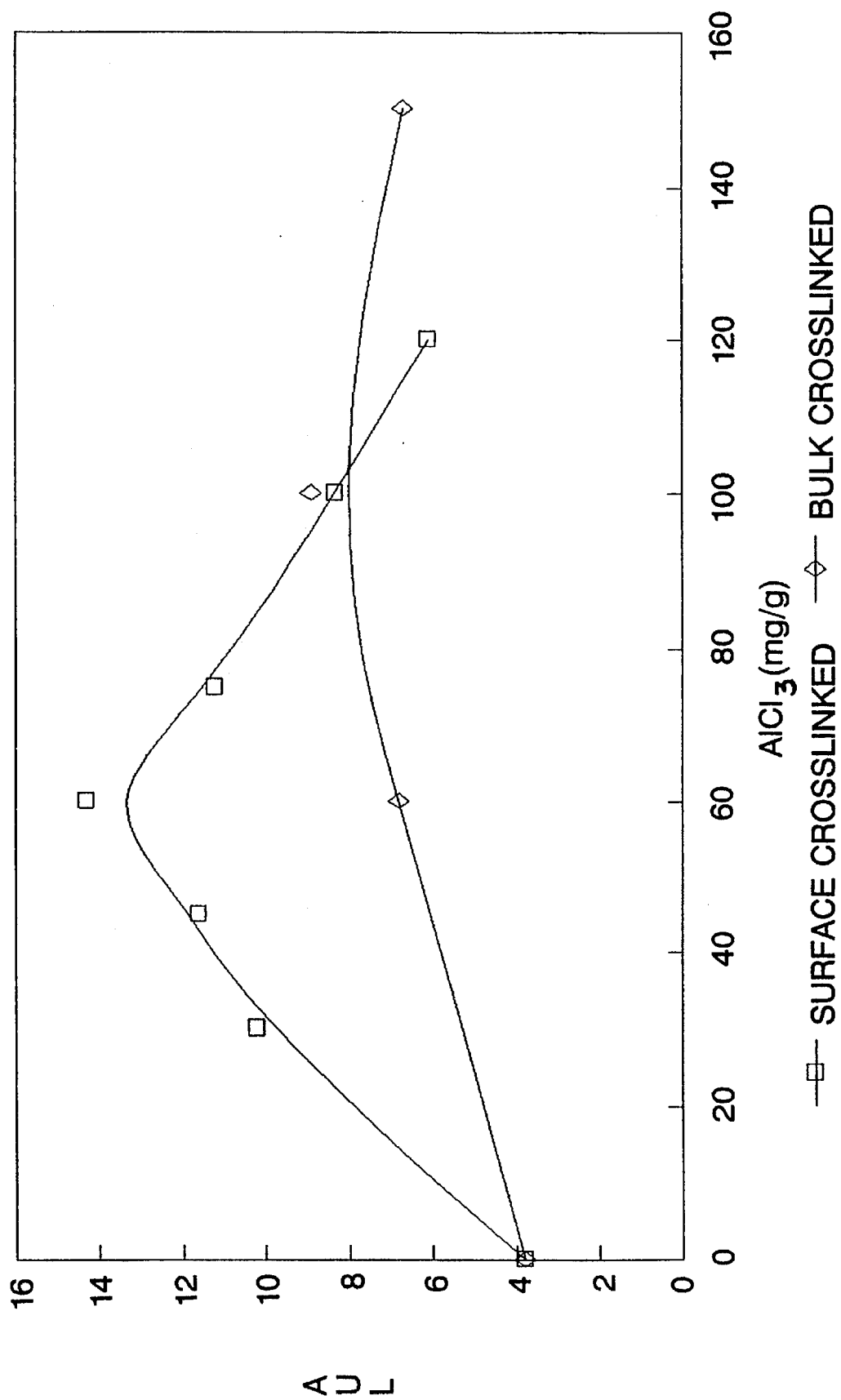

MODIFIED POLYSACCHARIDES HAVING IMPROVED ABSORBENT PROPERTIES AND PROCESS FOR THE PREPARATION THEREOF

BACKGROUND OF THE INVENTION

This application is a divisional application of application Ser. No. 08/116,180 filed on Sep. 2, 1993, now U.S. Pat. No. 5,470,964, which is a continuation-in-part of U.S. Ser. No. 07/837,304, filed Feb. 14, 1992, now abandoned.

FIELD OF THE INVENTION

The present invention relates to modified polysaccharides having improved absorbent properties. Specifically, the present invention relates to a surface-crosslinked, modified polysaccharide having the ability to absorb liquid while under a load and a process for the preparation thereof.

DESCRIPTION OF THE RELATED ART

The use of absorbent materials, commonly known as superabsorbents, in disposable absorbent personal care products is known. Such absorbent materials are generally employed in absorbent products, such as diapers, training pants, adult incontinence products, feminine care products, and the like, in order to increase the absorbent capacity of such products while reducing their overall bulk. Such absorbent materials are generally present in absorbent products in a fibrous matrix, such as a matrix of wood pulp fluff. A matrix of wood pulp fluff generally has an absorbent capacity of about 6 grams of liquid per gram of fluff. The absorbent materials described above generally have an absorbent capacity of at least about 10, preferably of about 20, and often up to about 100 times their weight in water. Clearly, incorporation of such absorbent materials in personal care products can reduce the overall bulk while increasing the absorbent capacity of such products.

A wide variety of materials has been described for use as absorbent materials in such personal care products. Such materials include natural-based materials, such as agar, pectin, gums, carboxyalkyl starch, carboxyalkyl cellulose, and the like; as well as synthetic materials, such as polyacrylates, polyacrylamides, hydrolyzed polyacrylonitrile, and the like. While natural-based absorbent materials are known for use in personal care products, they have not gained wide usage in such products, at least in part, because their absorbent properties are generally inferior compared to synthetic absorbent materials, such as the polyacrylates. Specifically, many of the natural-based materials tend to form soft, gelatinous masses when swollen with a liquid. When employed in absorbent products, the presence of such soft, gelatinous masses tends to prevent the transport of liquid within the fibrous matrix in which the absorbent materials are incorporated. This phenomenon is known as gel blocking. Once gel blocking occurs, subsequent insults of liquid cannot be efficiently absorbed by the product, and the product tends to leak. Further, many of the natural-based materials exhibit poor absorption properties, particularly when subjected to external pressures. In contrast, the synthetic, absorbent materials are often capable of absorbing large quantities of liquids while maintaining a generally stiff, non-gelatinous character. Accordingly, the synthetic absorbent materials can be incorporated in absorbent products while minimizing the likelihood of gel blocking.

A number of approaches have been suggested to improve the liquid absorptive and retentive properties of various natural-based absorbent materials. For example, U.S. Pat. No. 3,723,413 issued Mar. 27, 1973, to Chatterjee et al. describes the heat treatment of a carboxyalkyl cellulose in the presence of remaining carboxyalkylating reactants and byproducts, such that the carboxyalkyl cellulose becomes water insoluble and possessed of desirable liquid absorptive and retentive properties and characteristics.

U.S. Pat. No. 3,379,720 issued Apr. 23, 1968, to Reed describes a process of preparing modified polysaccharides, such as ethers and esters of cellulose, comprising slurrying a water-soluble polysaccharide in an inert medium, acidifying said polysaccharide, removing excess acid from the acidified polysaccharide, drying same and heat curing.

U.S. Pat. No. 4,689,408 issued Aug. 25, 1987, to Gelman et al. describes a method of preparing salts of carboxymethyl cellulose. The method involves treating a carboxymethyl cellulose with water, adding a nonsolvent for the carboxymethyl cellulose, and recovering the carboxymethyl cellulose. The carboxymethyl cellulose is said to have an absorbency of at least 25 grams of liquid per gram of carboxymethyl cellulose.

The natural-based polysaccharide materials are often water soluble. Accordingly, it is necessary to render the materials generally water insoluble when the materials are intended for use in personal care products. Many known methods of introducing a degree of water insolubility into absorbent materials involve the bulk crosslinking of the absorbent material. Unfortunately, such bulk-crosslinked absorbent materials are not always possessed of desirable liquid-absorbent and retentive properties. In an attempt to improve these properties, several surface-treating processes have been suggested.

U.S. Pat. No. 4,043,952 issued Aug. 23, 1977, to Ganslaw et al. is directed to a surface-treatment process for improving dispersibility of an absorbent composition. Disclosed is a means of improving the aqueous dispersibility of a water-absorbent composition, through the use of a surface treatment which, ionically, complexes the surface thereof to a moderate degree.

U.S. Pat. No. 4,666,983 issued May 19, 1987, to Tsubakimoto et al. is directed to an absorbent article. The absorbent article is obtained by mixing 100 parts by weight of an absorbent resin powder having a carboxyl group with a crosslinking agent having at least two functional groups capable of reacting with a carboxyl group. The absorbent resin powder is said to become crosslinked at least in the vicinity of the surface of the absorbent resin powder.

U.S. Pat. No. 5,026,800 issued Jun. 25, 1991, to Kimura et al. is directed to a water-absorbent resin and production process. Disclosed is a water-absorbent resin prepared by polymerizing an aqueous solution of a water-soluble, ethylenically-unsaturated monomer, pulverizing and sieving the gel-like polymer so obtained, and crosslinking the surface of the polymer powder.

SUMMARY OF THE INVENTION

It is desirable to develop and produce a natural-based absorbent material having absorptive properties similar to synthetic, highly absorbent materials and, thus, suited for use in personal care absorbent products.

The present invention concerns a method for producing a surface-crosslinked, modified polysaccharide. The method comprises the step of forming a mixture comprising water and a crosslinking agent. A generally water-soluble, modified polysaccharide is then added to the mixture, wherein the surface of the modified polysaccharide becomes crosslinked. The water-soluble, modified polysaccharide is swellable in the mixture. The modified polysaccharide is then dried.

The present invention further concerns a surface-crosslinked, modified polysaccharide. The surface-crosslinked, modified polysaccharide comprises a substantially non-crosslinked, generally water-soluble, modified polysaccharide core. Surrounding the core is a crosslinked, generally water-insoluble, modified polysaccharide shell.

BRIEF DESCRIPTION OF THE DRAWINGS

FIG. 2 illustrates, in the form of a graph, the results of the physical property testing set forth in Table 1.

DETAILED DESCRIPTION OF THE PREFERRED EMBODIMENT

Figure 1:
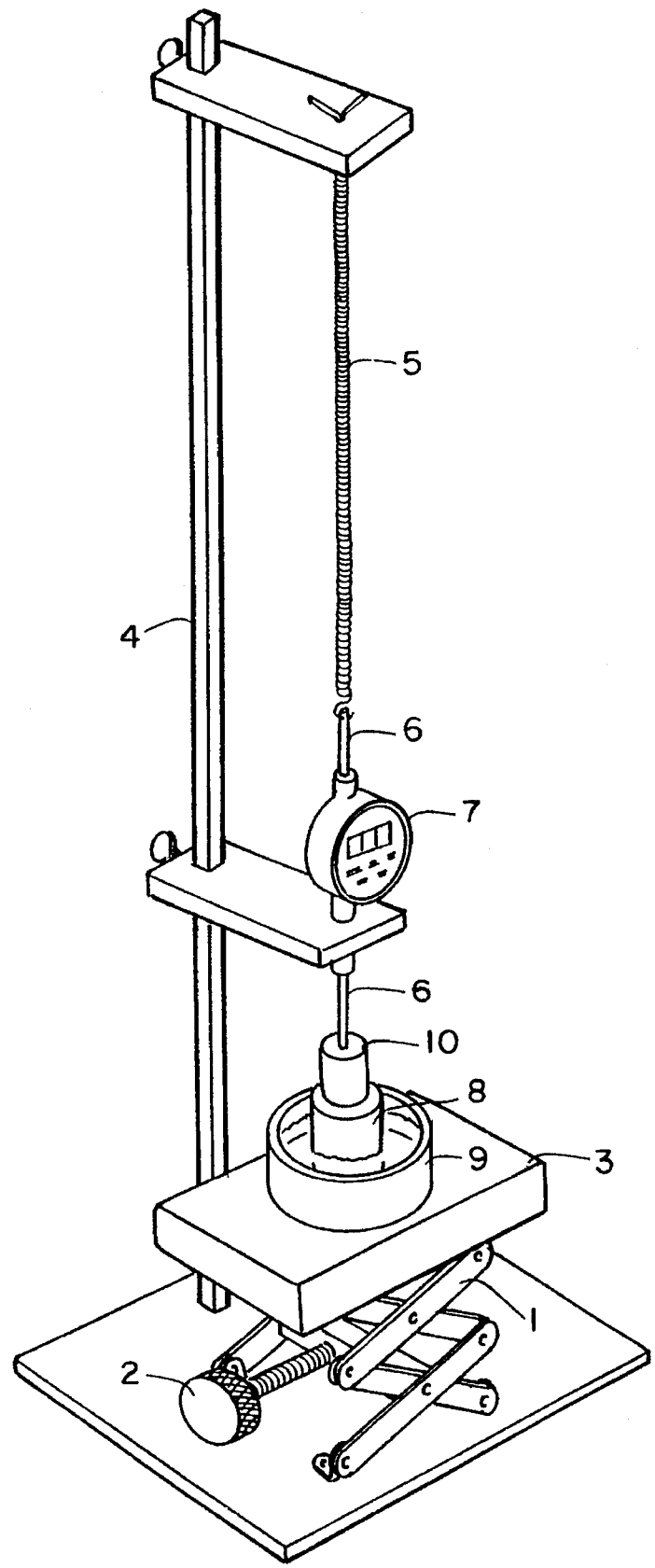
FIG. 1 illustrates the apparatus for determining the Absorbency Under Load values of an absorbent material.

In one aspect, the present invention concerns a method for producing a surface-crosslinked, modified polysaccharide. The method comprises the steps of forming a mixture comprising water and a crosslinking agent. A generally water-soluble, modified polysaccharide is then added to the mixture comprising water and a crosslinking agent. The water-soluble, modified polysaccharide absorbs at least a portion of the water and crosslinking agent mixture, and the surface of the modified polysaccharide becomes crosslinked. The modified polysaccharide is then dried.

Modified polysaccharides, suitable for use in the present invention, are generally water soluble. As used herein, a modified polysaccharide will be considered to be water soluble when it either dissolves in water to form a true solution or swells in water to such an extent that it appears to lose its initial structure even though a true solution may not be formed. As a general rule, the water-soluble, modified polysaccharides will be free from a substantial degree of crosslinking, as crosslinking tends to render the modified polysaccharides water insoluble.

Modified polysaccharides suitable for use in the present invention include, without limitation, the carboxylated, sulfonated, sulfated, and phosphated derivatives of polysaccharides, their salts, and mixtures thereof. Exemplary of suitable polysaccharides are cellulose, starch, carrageenan, agar, gellan gum, chitin, and the like, and mixtures thereof. The preferred modified polysaccharide is a carboxyalkyl polysaccharide such as a carboxyalkyl cellulose, for example, carboxymethyl cellulose, carboxyethyl cellulose, or the like.

When the modified polysaccharide is a carboxyalkyl cellulose, the carboxyalkyl cellulose suitably has an average degree of substitution of from about 0.3 to about 1.5, preferably from about 0.4 to about 1.2. The degree of substitution refers to the average number of carboxyl groups present on the anhydroglucose unit of the cellulosic material. When the carboxyalkyl cellulose has an average degree of substitution greater than about 0.3, the carboxyalkyl cellulose is generally water soluble.

When the modified polysaccharide is a carboxyalkyl cellulose, those carboxyalkyl celluloses having a relatively high molecular weight are generally preferred for use in the present invention. Nonetheless, a broad range of molecular weights are suitable for use in the present invention. It is generally most convenient to express the molecular weight of carboxyalkyl cellulose in terms of its viscosity in a 1.0 weight percent aqueous solution at 25° C. Carboxymethyl celluloses suitable for use in the present invention will generally have a viscosity in a 1.0 weight percent aqueous solution at 25° C. of from about 10 centipoise to about 40,000 centipoise or higher, preferably from about 500 centipoise to about 40,000 centipoise, and most preferably from about 1000 centipoise to about 40,000 centipoise.

Preferred carboxyalkyl celluloses have a relatively high degree of substitution and a relatively high molecular weight.

It is generally preferred that the modified polysaccharides be relatively dry when employed in the process of the present invention. It is, however, not necessary that the modified polysaccharide be completely water free. In fact, modified polysaccharides may contain a relatively high weight percent of water prior to the addition of the modified polysaccharide to the mixture of water and crosslinking agent and still be suited for use in the present invention. For example, commercially available carboxymethyl cellulose generally comprises about 8 weight percent water. Applicant has found that, at water concentrations greater than about 500 weight percent (5 grams of water per gram of modified polysaccharide prior to the addition of the modified polysaccharide to a mixture of water and crosslinking agent), the performance of the surface-crosslinked, modified polysaccharides is deleteriously affected.

Modified polysaccharides, in a wide variety of shapes, may be employed in the process of the present invention. Specifically, it is possible for the modified polysaccharide to be in the form of individual particles, flakes, films, fibers, and the like. When the modified polysaccharide is a carboxyalkyl cellulose, suitable carboxyalkyl celluloses are commercially available from a number of commercial sources. Exemplary of such a commercially available carboxyalkyl cellulose is a carboxymethyl cellulose commercially available from Aqualon Company under the trade designation AQUALON™ or BLANOSE™ cellulose gum.

Crosslinking agents suitable for use in the present invention are generally water soluble and comprise a compound having at least two functional groups or functionalities capable of reacting in an aqueous solution with the carboxyl, hydroxyl, and/or amino groups of a modified polysaccharide. The crosslinking agent is suitably selected from the group consisting of metal cations having a valency of at least 3; organic compounds comprising at least two, preferably at least four, carbon atoms and having at least two functional groups or functionalities capable of reacting in an aqueous solution with the carboxyl, hydroxyl, and/or amino group of a modified polysaccharide; phosphoryl chloride; and phosphoryl bromide. Examples of suitable organic crosslinking agents include dialdehydes, dianhydrides, polyamines, polyacids, succinyl dichloride, and the like, and mixtures thereof. Suitable metal cations having a valency of 3 or greater include those of aluminum, chromium, cerium, zirconium, cobalt and the like, and mixtures thereof. The preferred crosslinking agent is an aluminum cation having a valency of 3.

Without intending to be bound thereby, Applicant hypothesizes that it is desirable to employ a metal cation having a valency of at least 3 to encourage intermolecular bonding between adjacent polymeric chains. Applicant has found that crosslinking with a divalent metal ion appears to encourage intramolecular bonding within a single polymer chain rather than intermolecular bonding between adjacent polymer chains. When intramolecular bonding occurs, the improvement in liquid absorptive and retentive properties is not as marked as when intermolecular bonding occurs.

Those skilled in the art will recognize that, when the crosslinking agent is a metal cation having a valency of at least 3, the metal cation will generally be provided in the form of an electrolyte capable of disassociating, in water, into ions. For example, when aluminum cation is the crosslinking agent, the aluminum cation will often be supplied in the form of an electrolyte, such as aluminum chloride ($AlCl_3$), aluminum sulfate ($Al_2(SO_4)_3$), aluminum acetate ($Al(CH_3COO)_3$), or the like.

A mixture comprising water and the crosslinking agent is formed. As the crosslinking agent is generally water soluble, it disperses upon forming the mixture comprising water and the crosslinking agent. In addition to water and the crosslinking agent, the mixture may comprise a variety of other materials so long as they do not interfere with the surface crosslinking described herein. For example, the mixture may comprise up to about 90 weight percent of an inert solvent, such as an alcohol, acetone, or the like. As a general rule, the mixture comprises at least about 50 weight percent water, beneficially at least about 75 weight percent, preferably at least about 90 weight percent water, and most preferably about 95 weight percent water. The crosslinking agent is present in the mixture in an effective amount. That is, the crosslinking agent is present in an amount sufficient to provide the desired degree of crosslinking. The exact amount of crosslinking agent will, of course, depend on the exact crosslinking agent employed. As a general rule, the crosslinking agent will be present in an amount of from about 0.001 to about 10 weight percent, preferably of from about 0.1 to about 5.0 weight percent, based on total mixture weight. As a general rule, the amount of crosslinking agent will affect the degree or density of crosslinking that occurs in the crosslinked shell of the modified polysaccharide. As such, a lesser amount of crosslinking agent will generally result in less crosslinking of the crosslinked shell of the modified polysaccharide, whereas relatively more of a crosslinking agent will result in more crosslinking of the crosslinked shell of the modified polysaccharide.

The amount of crosslinking agent present in the mixture, in order to optimize the absorbent properties of the modified polysaccharide, depends on a variety of factors. For example, when an aluminum cation is the crosslinking agent, if the aluminum cation is supplied in the form of aluminum chloride, a lower weight amount of aluminum chloride can be used than if the aluminum cation is supplied in the form of a hydrate of aluminum sulfate. This is because the molecular weight of aluminum sulfate is greater than that of aluminum chloride. In order to provide the equivalent number of aluminum ions for crosslinking, a greater weight of aluminum sulfate will be necessary (compared to aluminum chloride). One skilled in the art can easily experimentally determine the optimum amount of a given crosslinking agent employed in surface crosslinking a given modified polysaccharide.

Any temperature. at which the mixture can be formed is believed suitable for use in the present invention. The mixture is preferably formed with agitation.

The modified polysaccharide is then added to the mixture comprising water and the crosslinking agent. The amount of polysaccharide material added to the mixture is sufficient to bring the weight ratio of modified polysaccharide to water (in the mixture) to from about 1:1 to about 1:40, beneficially from about 1:1 to about 1:20, preferably from about 1:1 to about 1:10, and most preferably of from about 1:2 to about 1:5.

When the water-soluble, modified polysaccharide is added to the mixture comprising water, the water present in the mixture penetrates and softens at least a portion of the outer surface of the modified polysaccharide material. That is, the water present in the mixture is functionally absorbed by the modified polysaccharide. As the crosslinking agent is soluble in the water, the crosslinking agent is similarly brought into the modified polysaccharide material. The crosslinking agent reacts in the mixture with the modified polysaccharide such that the surface of the modified polysaccharide becomes crosslinked.

Applicant hypothesizes that the ratio of modified polysaccharide to water determines the depth to which the crosslinking agent (and subsequently the crosslinking) penetrates the modified polysaccharide. If the ratio of modified polysaccharide to water is less than about 1:1, the water is not present in an amount sufficient to penetrate the modified polysaccharide to any significant degree. It follows that the crosslinking would occur only on the very surface of the modified polysaccharide. In this instance, the depth of crosslinking may be so minimal as to be insufficient to provide the desired absorbent properties of the modified polysaccharide. As a general rule, an insufficient depth or amount of crosslinking of the modified polysaccharide results in the crosslinking not being of a sufficient strength to maintain the desired absorbent properties of the modified polysaccharide when the modified polysaccharide is employed in a desired use, such as a superabsorbent material.

Correspondingly, if the ratio of modified polysaccharide to water is greater than about 1:40, there is so much water that it penetrates into substantially the entire amount of the modified polysaccharide. The crosslinking which occurs is effectively a bulk-crosslinking process (generally uniform crosslinking throughout the modified polysaccharide) rather than a surface-crosslinking process. Again, this does not generally lead to optimized absorption properties.

After the modified polysaccharide has been added to the mixture of water and crosslinking agent, the modified polysaccharide is dried. Such drying helps to increase the stability or strength of the surface crosslinking of the modified polysaccharide. The drying can occur under any conditions sufficient to cause the desired degree of drying without degrading or otherwise deleteriously affecting the absorbent properties of the modified polysaccharide. Suitably, the modified polysaccharide is dried at an elevated temperature within the range of from about 25° C. to about 250° C. Applicant hypothesizes that it is desirable to dry a sufficient amount of water from the modified polysaccharide to bring the polymeric chains close enough together to strengthen the intermolecular crosslinking that occurred in the mixture. How much drying needs to occur, in order to achieve such stabilizing or strengthening of the surface crosslinking, will depend on the crosslinking agent employed, the ratio of modified polysaccharide to water, and the composition of the modified polysaccharide. Nonetheless, it is important that sufficient drying occurs to achieve the desired stabilizing or strengthening of the surface crosslinking. The degree of drying may range from removal of practically no moisture to removal of practically all the moisture present in the polysaccharide.

In one preferred embodiment, the modified polysaccharide is a carboxyalkyl cellulose, such as carboxymethyl cellulose. The crosslinking agent employed is a metal cation having a valency of 3 or greater. The crosslinking agent is dissolved in water to form a mixture. The carboxymethyl cellulose is added to the mixture in a weight ratio of carboxymethyl cellulose to water of from about 1:1 to about 1:10. The water and crosslinking agent is absorbed into the outer surface of the carboxymethyl cellulose. The carboxymethyl cellulose is subsequently dried to remove at least about 50, preferably about 75, and most preferably about 90 weight percent of the water originally present in the mixture which was absorbed by the carboxymethyl cellulose.

The surface crosslinking of the modified polysaccharide produces a modified polysaccharide which is generally water insoluble. That is, the outer surface of the modified polysaccharide is rendered generally water insoluble due to the crosslinking introduced by the described method.

The described method produces a surface-crosslinked, modified polysaccharide having an improved ability to absorb a liquid while under a load compared to the starting, nonsurface-crosslinked, modified polysaccharide. The method by which the Absorbency Under Load is determined is set forth below in connection with the examples. The Absorbency Under Load values, determined as set forth below and reported herein, refer to the amount, in grams, of an aqueous solution containing 0.9 weight percent sodium chloride a gram of the material being tested can absorb in 60 minutes under a load of about 0.3 pound per square inch. As used herein, the term "initial Absorbency Under Load" is meant to refer to that AUL exhibited by a modified polysaccharide stored at ambient conditions, such as about 24° C. and 0% relative humidity, as measured within 1 day after preparation of the modified polysaccharide, such as by the methods described in this invention to provide a modified polysaccharide with effective surface crosslinking and the desired absorbency properties of this invention.

As a general rule, it is desired that the surface-crosslinked, modified polysaccharides of the present invention have an initial Absorbency Under Load value which is at least about 200 percent, beneficially at least about 250 percent, most beneficially at least about 300 percent, and preferably at least about 400 percent greater than the initial Absorbency Under Load value of the starting, nonsurface-crosslinked, modified polysaccharide. That is, if the modified polysaccharide is carboxymethyl cellulose, the surface-crosslinked, carboxymethyl cellulose formed by the described method has an initial Absorbency Under Load value which is at least about 200 percent greater than the same (starting) carboxymethyl cellulose which has not been surface crosslinked.

When the modified polysaccharide is a carboxymethyl cellulose having a viscosity (one weight percent aqueous solution at 25° C.) of at least about 2000 centipoise, the surface-crosslinked, carboxymethyl cellulose suitably has an Absorbency Under Load value of at least about 8, beneficially of at least about 10, most beneficially of at least about 12, and preferably at least about 16. The carboxymethyl cellulose, prior to surface crosslinking according to the present invention has an Absorbency Under Load value of about 3.8 grams. Synthetic polymeric materials, such as polyacrylates having a generally high ability to absorb while under a load, have been found to minimize the occurrence of gel blocking when incorporated in absorbent products.

In another aspect, the present invention relates to a surface-crosslinked, modified polysaccharide. The surface-crosslinked, modified polysaccharide is generally water swellable and generally water insoluble. The surface-crosslinked, modified polysaccharide comprises a substantially non-crosslinked, generally water-soluble, modified polysaccharide core and a crosslinked, generally water-insoluble, modified polysaccharide shell at least partially surrounding the core. In a preferred embodiment, the shell is effective to increase the Absorbency Under Load of the surface-crosslinked, modified polysaccharide by at least about 200 percent, beneficially at least about 250 percent, most beneficially at least about 300 percent, and preferably at least about 400 percent compared to an identical substantially non-crosslinked, generally water-soluble, modified polysaccharide. That is, if the modified polysaccharide is carboxymethyl cellulose, the carboxymethyl cellulose having a crosslinked shell has an Absorbency Under Load value which is at least about 200 percent larger than the Absorbency Under Load value of the carboxymethyl cellulose from which the surface-crosslinked, carboxymethyl cellulose is formed.

It is preferred that the core and shell be formed from the same base modified polysaccharide having different levels of crosslinking. The described surface-crosslinked, modified polysaccharide is suitably formed by the method described above. Nonetheless, the described method is not intended to be the exclusive method by which the surface-crosslinked, modified polysaccharide can be formed. It is preferred that the crosslinked, generally water-insoluble, modified polysaccharide shell substantially completely surrounds the substantially non-crosslinked, generally water-soluble, modified polysaccharide core and be effective to increase the Absorbency Under Load value of the surface-crosslinked, modified polysaccharide by at least about 200 percent compared to an identical substantially non-crosslinked, generally water-soluble, modified polysaccharide.

The modified polysaccharides of the present invention are suitable for use in personal care products, such as diapers, training pants, feminine care products, adult incontinence products, wound dressings, and the like.

TEST METHODS

Absorbency Under Load

The Absorbency Under Load (AUL) is a test which measures the ability of an absorbent material to absorb a liquid (0.9 weight percent solution of sodium chloride in distilled water) while under an applied load or restraining force.

Referring to FIG. 1, the apparatus and method for determining AUL will be described. Shown is a perspective view of the apparatus in position during a test. Shown is a laboratory jack 1 having an adjustable knob 2 for raising and lowering the platform 3. A laboratory stand 4 supports a spring 5 connected to a modified thickness meter probe 6, which passes through the housing 7 of the meter, which is rigidly supported by the laboratory stand. A plastic sample cup 8, which contains the superabsorbent material sample to be tested, has a liquid-permeable bottom and rests within a Petri dish 9 which contains the saline solution to be absorbed. A weight 10 rests on top of a spacer disc (not visible) resting on top of the superabsorbent material sample (not visible).

The sample cup consists of a plastic cylinder having a 1 inch inside diameter and an outside diameter of 1.25 inches. The bottom of the sample cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder.

The modified thickness meter used to measure the expansion of the sample while absorbing the saline solution is a Mitutoyo Digimatic Indicator, IDC Series 543, Model 543-180, having a range of 0–0.5 inch and an accuracy of 0.00005 inch (Mitutoyo Corporation, 31-19, Shiba 5-chome, Minato-ku, Tokyo 108, Japan). As supplied from Mitutoyo Corporation, the thickness meter contains a spring attached to the probe within the meter housing. This spring is removed to provide a free-falling probe which has a downward force of about 27 grams. In addition, the cap over the top of the probe located on the top of the meter housing is also removed to enable attachment of the probe to the suspension spring 5 (available from McMaster-Carr Supply Co., Chicago, Illinois, Item No. 9640K41), which serves to counter or reduce the downward force of the probe to about 1 gram, ±0.5 gram. A wire hook can be glued to the top of the probe for attachment to the suspension spring. The bottom tip of the probe is also provided with an extension needle (Mitutoyo Corporation, Part No. 131279) to enable the probe to be inserted into the sample cup.

To carry out the test, a 0.160 gram sample of the absorbent material, which has been sieved to a particle size between 300 and 600 microns, is placed into the sample cup. The sample is then covered with a plastic spacer disc, weighing 4.4 grams, which is slightly smaller than the inside diameter of the sample cup and serves to protect the sample from being disturbed during the test. The 100 gram weight is then placed on top of the spacer disc, thereby applying a load of 0.3 pound per square inch. The sample cup is placed in the Petri dish on the platform of the laboratory jack raised up until it contacts the tip of the probe. The meter is zeroed. A sufficient amount of saline solution is added to the Petri dish (50–100 milliliters) to begin the test. The distance the weight is raised by the expanding sample, as it absorbs the saline solution, is measured by the probe. This distance, multiplied by the cross-sectional area inside the sample cup, is a measure of the expansion volume of the sample due to absorption. Factoring in the density of the saline solution and the weight of the sample, the amount of saline solution absorbed is readily calculated. The weight of saline solution absorbed after 60 minutes is the AUL value expressed as grams saline solution absorbed per gram of absorbent. If desired, the readings of the modified thickness meter can be continuously input to a computer (Mitutoyo Digimatic Miniprocessor DP-2 DX) to make the calculations mnd provide AUL readings. As a cross-check, the AUL can also be determined by determining the weight difference between the sample cup before and after the test, the weight difference being the amount of solution absorbed by the sample.

EXAMPLES

Example 1

A sodium carboxymethyl cellulose, commercially available from the Aqualon Company under the trade designation AQUALON™ Cellulose Gum CMC-7HCF, is provided. The carboxymethyl cellulose has an average degree of substitution of 0.7. Ten grams of the carboxymethyl cellulose is added to an aqueous solution containing 40 grams of distilled water and 0.3 gram of aluminum chloride. The carboxymethyl cellulose "absorbs" the aqueous mixture. The carboxymethyl cellulose is then dried in a Blue M air convection oven at a temperature of about 80° C. for about five hours. After drying, the carboxymethyl cellulose is subjected to Absorbency Under Load testing. The carboxymethyl cellulose so formed is found to have an AUL value of about 16.6 g/g. A control sample of the carboxymethyl cellulose (AQUALON™ Cellulose Gum CMC-7HCF) is also subjected to Absorbency Under Load testing in the form in which it is commercially received. The control carboxymethyl cellulose is found to have an AUL value of about 3.8 g/g.

It is seen that the surface crosslinking of the present invention produces a carboxymethyl cellulose having a dramatically improved AUL value (16.6) compared to the non-crosslinked control (3.8).

Example 2

A surface-crosslinked, sodium carboxymethyl cellulose is prepared as set forth in Example 1 with the exception that the amount of aluminum chlortie present in the aqueous mixture ts varied. Specifically, the milligrams of aluminum chloride per gram of sodium carboxymethyl cellulose is varied from 0 milligrams per gram of carboxymethyl cellulose (control) to 120 milligrams per gram of carboxymethyl cellulose. The resultant surface-crosslinked, carboxymethyl celluloses are subjected to Absorbency Under Load testing.

A bulk-crosslinked comparison sample is prepared using the same carboxymethyl cellulose as in Example 1. The bulk-crossltnked material is prepared by dissolving 1 gram of carboxymethyl cellulose in 2,000 grams of distilled water. An amount of aluminum chloride from 0 milligram per gram of carboxymethyl cellulose to 150 milligrams per gram of carboxymethyl cellulose is added to the aqueous solution of carboxymethyl cellulose. The carboxymethyl cellulose is recovered by drying (<5 percent moisture content) and is subjected to Absorbency Under Load testing. The results of this testing are set forth in Table 1 and are graphically illustrated in FIG. 2.

TABLE 1

| AlCl$_3$ (mg/g) | AUL (g/g) | |
|---|---|---|
| | Surface Crosslinked | Bulk Crosslinked* |
| 0* | 3.8 | 3.8 |
| 30 | 10.2 | |
| 45 | 11.6 | |
| 60 | 14.3 | 6.8 |
| 75 | 11.2 | |
| 100 | 8.3 | 8.9 |
| 120 | 6.1 | |
| 150 | | 6.7 |

*Not an example of the present invention

As can be seen from reference to Table 1 and FIG. 2, the surface crosslinking of the present invention improves the AUL values compared to a bulk-crosslinking process at equivalent crosslinking agent concentrations over a wide range of crosslinking agent concentrations. As may be seen from Table 1, however, if too high of a crosslinking agent concentration is used for a particular crosslinking agent, the degree of surface crosslinking of the modified polysaccharide achieved may be so high as to result in undesirable absorbent properties.

Example 3

Surface-crosslinked, sodium carboxymethyl celluloses are prepared according to the method of Example 1 with the exception that different crosslinking agents in varying amounts are employed. The crosslinking agent, and the form in which it is supplied, and its concentration in millimoles per gram of sodium carboxymethyl cellulose and milligrams per gram of sodium carboxymethyl cellulose, are set forth in Table 2. These surface-crosslinked, carboxymethyl celluloses so produced are subjected to AUL testing and the results are also set forth in Table 2. Control samples employing crosslinking agents of metal cations having a valency of 2 are also produced. These control samples are subjected to AUL testing and the results set forth in Table 2.

TABLE 2

| Crosslinking Agent | Molecular Weight | mMol/g | mg/g | AUL (g/g) |
|---|---|---|---|---|
| $AlCl_3$ | 133.5 | 0.225[1] | 30 | 14.6 |
| $Al_2(SO_4)_3 \cdot 14H_2O$ | 594.0 | 0.265 | 155 | 8.1 |
|  |  | 0.225 | 134 | 9.8 |
|  |  | 0.150 | 90 | 10.3 |
|  |  | 0.112[1] | 65 | 13.2 |
| $Ce(NH_4)_4(SO_4)_4 \cdot 2H_2O$ | 632.1 | 0.225 | 142 | 10.0 |
|  |  | 0.190 | 120 | 11.2 |
|  |  | 0.169[1] | 106 | 8.7 |
| $ZnCl_2$* | 136.3 | 0.338[1] | 46 | 4.6 |
| $CaCl_2 \cdot 2H_2O$* | 147.0 | 0.338[1] | 50 | 4.1 |

*Not an example of the present invention
[1]"Underlinking" indicates that the carboxymethyl cellulose is crosslinked by the same number of positive charges per gram of carboxymethyl cellulose.

Reference to Table 2 or tetravalent metal cations, such as those of aluminum and cesium, produce higher AUL values than divalent cations, such as those of zinc and calcium, at equivalent positive charges per gram of carboxymethyl cellulose.

Example 4

Commercially available sodium carboxymethyl celluloses, available from the Aqualon Company, are provided. The sodium carboxymethyl cellulose materials have varying molecular weights, as reflected in viscosity of a 1 weight percent solution at 25° C., and varying degrees of substitution. Ten grams of the various carboxymethyl cellulose are added to an aqueous solution containing 40 grams of distilled water and 0.3 gram of aluminum chloride (0.6 gram of aluminum chloride are used for the CMC-9H4F). The carboxymethyl cellulose absorbs the water and is then dried in a Blue M air convection oven at 80° C. for five hours. The exact degree of substitution and molecular weight, as reflected in viscosity, is set forth in Table 3. The samples thus prepared are subjected to AUL testing and the results set forth in Table 3. Control samples of each of the commercially available carboxymethyl cellulose materials are also subjected to AUL testing and the results set forth in Table 3.

TABLE 3

| Aqualon Trade designation | Viscosity (cps) | Degree of Substitution | AUL (g/g) Control | AUL (g/g) Crosslinked |
|---|---|---|---|---|
| CMC-7H | 1,500–3,000 | 0.65–0.95 | 3.7 | 14.2 |
| CMC-7HCF | 1,000–2,800 | 0.65–0.95 | 3.1 | 12.6 |
| CMC-7H4F | 2,500–6,000 | 0.65–0.95 | 4.6 | 16.5 |
| CMC-12M8 | 800–1,600 | 1.15–1.45 | 1.3 | 7.7 |
| CMC-9H4F | 2,500–6,000 | 0.80–0.95 | 4.4 | 14.3 |

As can be seen from reference to Table 4, higher molecular weight carboxymethyl cellulose generally produces higher AUL values.

Example 5

A sodium carboxymethyl cellulose, commercially available from the Aqualon Company under the trade designation AQUALON™ Cellulose Gum CMC-7HCF, is provided. The carboxymethyl cellulose has a particle size range of from 300 to 600 microns. Ten grams of the carboxymethyl cellulose, as commercially supplied, is first swollen with water in an amount of from 0 gram of water per gram of carboxymethyl cellulose to 20 grams of water per gram of carboxymethyl cellulose. The samples thus treated are then surface crosslinked by adding the carboxymethyl cellulose to a mixture comprising 40 grams of water and 0.3 gram of aluminum chloride. The carboxymethyl cellulose absorbs the mixture of water and aluminum chloride and is subsequently dried to a moisture content of less than about 5 weight percent. The surface-crosslinked, sodium carboxymethyl celluloses as thus prepared are subjected to AUL testing and the results set forth in Table 4.

TABLE 4

| Amount of Water[1] (g/g) | AUL (g/g) |
|---|---|
| 0 | 14.9 |
| 5 | 14.4 |
| 10 | 12.2 |
| 20 | 10.8 |

[1]Prior to surface crosslinking

As can be seen from reference to Table 4, the Absorbency Under Load values tend to decrease as the amount of water absorbed by the carboxymethyl cellulose prior to surface crosslinking increases.

While the present invention has been described in terms of the specific embodiments described above, numerous equivalent changes and modifications will be clear to those skilled in the art. Accordingly, the specific examples described and set forth above are not intended to limit, in any manner, the scope of the invention as set forth in the appended claims.

What is claimed is:

1. A crosslinked, modified polysaccharide formed by a method comprising the following steps:

forming a mixture comprising water and a crosslinking agent wherein the crosslinking agent is water soluble and comprises a compound having at least two functional groups or functionaities capable of reacting in an aqueous solution with a carboxyl, hydroxyl, or amino group of a modified polysaccharide;

adding to said mixture an amount of a water-soluble, modified polysaccharide, that is free from a substantial degree of crosslinking, such that the weiqht ratio of water-soluble, modified polysaccharide to water in said mixture is from about 1:2 to about 1:40, wherein said water-soluble, modified polysaccharide becomes crosslinked, and wherein said crosslinked, modified polysaccharide comprises a substantially non-crosslinked, water-soluble, modified polysaccharide core and a crosslinked, water-insoluble, modified polysaccharide shell at least partially surrounding said core, said crosslinked, modified polysaccharide being swellable in said mixture; and drying said crosslinked, modified polysaccharide, wherein said crosslinked, modified polysaccharide has an initial Absorbency Under Load at least about 200 percent greater than said water-soluble, modified polysaccharide.

2. A crosslinked, carboxyalkyl polysaccharide formed by a method comprising the following steps:

forming a mixture comprising at least about 75 weight percent water and an amount of a crosslinking agent effective to provide a desired degree of crosslinking, wherein the crosslinking agent is water soluble and comprises a compound having at least two functional groups or functionalities capable of reacting in an aqueous solution with a carboxyl, hydroxyl, or amino group of a modified polysaccharide;

adding to said mixture an amount of a water-soluble, carboxyalkyl polysaccharide, that is free from a substantial degree of crosslinking, said water-soluble, carboxyalkyl polysaccharide being added to said mixture such that the weight ratio of carboxyalkyl polysaccharide to water is from about 1:2 to about 1:40, wherein said carboxyalkyl polysaccharide becomes crosslinked and wherein said crosslinked, carboxyalkyl polysaccharide comprises a substantially non-crosslinked, water-soluble, carboxyalkyl polysaccharide core and a crosslinked, water-insoluble carboxyalkyl polysaccharide shell at least partially surrounding said crosslinked, carboxyalkyl polysaccharide being swellable in said mixture; and drying said crosslinked, carboxyalkyl polysaccharide, wherein said crosslinked, carboxyalkyl polysacharide has an initial Absorbency Under Load at least about 200 percent greater than said water-soluble, carboxyalkyl polysaccharide.

3. A crosslinked, modified polysaccharide, said modified polysacchadde comprising:

a substantially non-crosslinked, water-soluble, modified polysacchadde core; and a crosslinked, water-insoluble, modified polysacchadde shell at least partially surrounding said core, wherein said shell is effective to increase the initial Absorbency Under Load value of said crosslinked, modified polvsacchadde by at least about 200 percent compared to an identical substantially non-crosslinked, water-soluble, modified polysacchadde.

4. The crosslinked, modified polysaccharide according to claim 3 wherein said modified polysaccharide is selected from the group consisting of carboxylated, sulfonated, sulfated and phosphated derivatives of polysaccharides, their salts and mixtures thereof.

5. The crosslinked, modified polysaccharide according to claim 3 wherein said modified polysaccharide is selected from the group consisting of the carboxylated, sulfonated, sulfated and phosphated derivatives of cellulose, starch, carrageenan, agar, gellan gum, chitin, their salts and mixtures thereof.

6. The crosslinked, modified polysaccharide according to claim 3 wherein said modified polysaccharide is a carboxyalkyl polysaccharide.

7. The crosslinked, modified polysaccharide according to claim 6 wherein said carboxyalkyl polysaccharide is a carboxyalkyl cellulose.

8. The crosslinked, modified carboxyalkyl cellulose according to claim 7 wherein said carboxyalkyl cellulose is carboxymethyl cellulose.

9. The crosslinked, modified polysaccharide according to claim 9 wherein said shell is crosslinked with a metal cation having a valency of 3 or more.

10. The crosslinked, modified polysaccharide according to claim 3 wherein said core and said shell comprise the same modified polysaccharide having different levels of crosslinking.

11. The crosslinked, modified polysaccharide according to claim 3 wherein said shell is crosslinked with an aluminum cation.

12. The crosslinked, modified polysaccharide according to claim 3 wherein said crosslinked, modified polysaccharide has an initial Absorbency Under Load value of at least about 8.

13. The crosslinked, modified polysaccharide according to claim 1 wherein said modified polysaccharide is selected from the group consisting of carboxylated, sulfonated, sulfated and phosphated derivatives of polysaccharides, their salts and mixtures thereof.

14. The crosslinked, modified polysaccharide according to claim 13 wherein said modified polysaccharide is selected from the group consisting of the carboxylated, sulfonated, sulfated and phosphated derivatives of cellulose, starch, carrageenan, agar, gellan gum, chitin, their salts and mixtures thereof.

15. The crosslinked, modified polysaccharide according to claim 14 wherein said modified polysaccharide is a carboxyalkyl polysaccharide.

16. The crosslinked, modified polysaccharide according to claim 15 wherein said carboxyalkyl polysaccharide is a carboxyalkyl cellulose.

17. The crosslinked, carboxyalkyl cellulose according to claim 16 wherein said carboxyalkyl cellulose is carboxymethyl cellulose.

18. The crosslinked, modified polysaccharide according to claim 1 wherein said crosslinking agent is selected from the group consisting of an electrolyte comprising a metal cation having a valency of 3 or greater; organic compounds comprising at least two carbon atoms and having at least two functional groups or functionalities capable of reacting in an aqueous solution with the carboxyl, hydroxyl, or amino group of a modified polysaccharide; phosphoryl chloride; and phosphoryl bromide.

19. The crosslinked, modified polysaccharide according to claim 18 wherein said crosslinking agent is an electrolyte comprising a metal cation having a valency of 3 or more.

20. The crosslinked, modified polysaccharide according to claim 19 wherein said crosslinking agent comprises an aluminum cation.

21. The crosslinked, modified polysaccharide according to claim 1 wherein the weight ratio of water-soluble, modified polysaccharide to water is from about 1:2 to about 1:10.

22. The crosslinked, modified polysaccharide according to claim 21 wherein the weight ratio of water-soluble, modified polysaccharide to water is from about 1:2 to about 1:5.

23. The crosslinked, modified polysaccharide according to claim 1 wherein said crosslinked, modified polysaccharide is dried to remove at least about 50 weight percent of the water originally present in said mixture.

24. The crosslinked, modified polysaccharide according to claim 1 wherein said crosslinked, modified polysaccharide has an initial Absorbency Under Load value of at least about 8.

25. The crosslinked, carboxyalkyl polysaccharide according to claim 2 wherein said carboxyalkyl polysaccharide is selected from the group consisting of the carboxylated derivatives of cellulose, starch, carrageenan, agar, gellan gum, chitin, their salts and mixtures thereof.

26. The crosslinked, carboxyalkyl polysaccharide according to claim 25 wherein said carboxyalkyl polysaccharide is a carboxyalkyl cellulose.

27. The crosslinked, carboxyalkyl cellulose according to claim 26 wherein said carboxyalkyl cellulose is carboxymethyl cellulose.

28. The crosslinked, carboxyalkyl polysaccharide according to claim 2 wherein said crosslinking agent is selected from the group consisting of an electrolyte comprising a metal cation having a valency of 3 or greater; organic compounds comprising at least two carbon atoms and having at least two functional groups or functional ities capable of reacting in an aqueous solution with the carboxyl, hydroxyl, or amino group of a carboxyalkyl polysaccharide; phosphoryl chloride; and phosphoryl bromide.

29. The crosslinked, carboxyalkyl polysaccharide according to claim 28 wherein said crosslinking agent is an electrolyte comprising a metal cation having a valency of 3 or more.

30. The crosslinked, carboxyalkyl polysaccharide according to claim 29 wherein said crosslinking agent comprises an aluminum cation.

31. The crosslinked, carboxyalkyl polysaccharide according to claim 2 wherein the weight ratio of water-soluble, carboxyalkyl polysaccharide to water is from about 1:2 to about 1:10.

32. The crosslinked, carboxyalkyl polysaccharide according to claim 31 wherein the weight ratio of water-soluble, carboxyalkyl polysaccharide to water is from about 1:2 to about 1:5.

33. The crosslinked, carboxyalkyl polysaccharide according to claim 2 wherein said crosslinked, carboxyalkyl polysaccharide is dried to remove at least about 50 weight percent of the water originally present in said mixture.

34. The crosslinked carboxyalkyl polysaccharide according to claim 2 wherein said crosslinked, carboxyalkyl polysaccharide has an initial Absorbency Under Load value of at least about 8.

* * * * *